(12) United States Patent
Klose

(10) Patent No.: US 6,744,501 B2
(45) Date of Patent: Jun. 1, 2004

(54) METHOD OF ANALYZING SILICON-GERMANIUM ALLOYS AND APPARATUS FOR MANUFACTURING SEMICONDUCTOR LAYER STRUCTURES WITH SILICON-GERMANIUM ALLOY LAYERS

(75) Inventor: Manfred Klose, Stuttgart (DE)

(73) Assignee: Deutsches Zentrum fuer Luft-und Raumfahrt e.V., Cologne (DE)

( * ) Notice: Subject to any disclaimer, the term of this patent is extended or adjusted under 35 U.S.C. 154(b) by 41 days.

(21) Appl. No.: 10/247,269

(22) Filed: Sep. 18, 2002

(65) Prior Publication Data

US 2003/0081205 A1 May 1, 2003

(30) Foreign Application Priority Data

Sep. 19, 2001 (DE) .......................... 101 46 826

(51) Int. Cl.$^7$ ................................. G01J 3/44
(52) U.S. Cl. ......................... 356/301; 438/16
(58) Field of Search ............................. 356/301; 438/16

(56) References Cited

U.S. PATENT DOCUMENTS

| | | | |
|---|---|---|---|
| 4,835,059 A | 5/1989 | Kodato | |
| 5,116,121 A | 5/1992 | Knoll et al. | |
| 6,067,154 A | 5/2000 | Hossain et al. | |
| 6,081,328 A | 6/2000 | Eng | |
| 6,473,174 B1 * | 10/2002 | Ballast et al. | ................ 356/301 |
| 2002/0008192 A1 * | 1/2002 | Isomura | .................... 250/214.1 |

FOREIGN PATENT DOCUMENTS

| | | | | |
|---|---|---|---|---|
| DE | 36 28 513 | 6/1987 | | |
| DE | 294 784 | 10/1991 | | |
| DE | 198 40 197 | 3/2000 | | |
| EP | 0 445 520 | 9/1991 | | |
| EP | 0 781 990 | 7/1997 | | |
| GB | 2 206 688 | 1/1989 | | |
| GB | 2 241 606 | * 4/1991 | .......... H01L/21/36 | |
| WO | WO 01/04609 | 1/2001 | | |

OTHER PUBLICATIONS

Mooney, P.M., et al., "Raman Scattering Analysis of Relaxed $Ge_xSi_{1-x}$ Alloy Layers," *Applied Physics Lett.*, 62 (17), Apr. 26, 1993, pp. 2069–2071.

Tsang, J.C., et al., "Measurements of Alloy Composition and Strain in Thin $Ge_xSi_{1-x}$ Layers," *J. Applied Physics*, 75 (12), Jun. 15, 1994, pp. 8098–8108.

Dietrich, B., et al., "Raman Investigations of Elastic Strain Relief in $Si_{1-x}Ge_x$ Layers on Patterned Silicon Substrate," *J. Appl. Phys.*, 74 (12), Dec. 15, 1993, pp. 7223–7227.

Fowler, A.B., et al, "Analytical Technique for Probing and Controlling Gas Composition In Chemical Processes," *IBM Technical Disclosure Bulletin*, vol. 15, No. 12, May 1973, pp. 3885–3886.

Liu, R., et al., "Raman Spectroscopy of Epitaxial $Si/Si_{1-x}Ge_x$ Heterostructures," *Mat. Res. Soc. Symp. Proc.*, vol. 533, 1998, pp. 63–68.

(List continued on next page.)

*Primary Examiner*—F. L. Evans
*Assistant Examiner*—Kara Geisel
(74) *Attorney, Agent, or Firm*—Barry R. Lipsitz; Douglas M. McAllister

(57) ABSTRACT

In order to improve a method of analyzing Si—Ge alloys, with which a Raman spectrum of a sample is recorded and Raman frequencies and Raman intensities of the Si—Si modes and the Si—Ge modes of the alloy layer are evaluated, such that any strain and any Ge portion in an alloy layer can be ascertained in a simple and as exact a manner as possible, it is provided for one or more spectrum contributions lying outside the Si—Ge modes and the Si—Si modes to be evaluated as oscillation modes.

23 Claims, 5 Drawing Sheets

OTHER PUBLICATIONS

Figure 1:
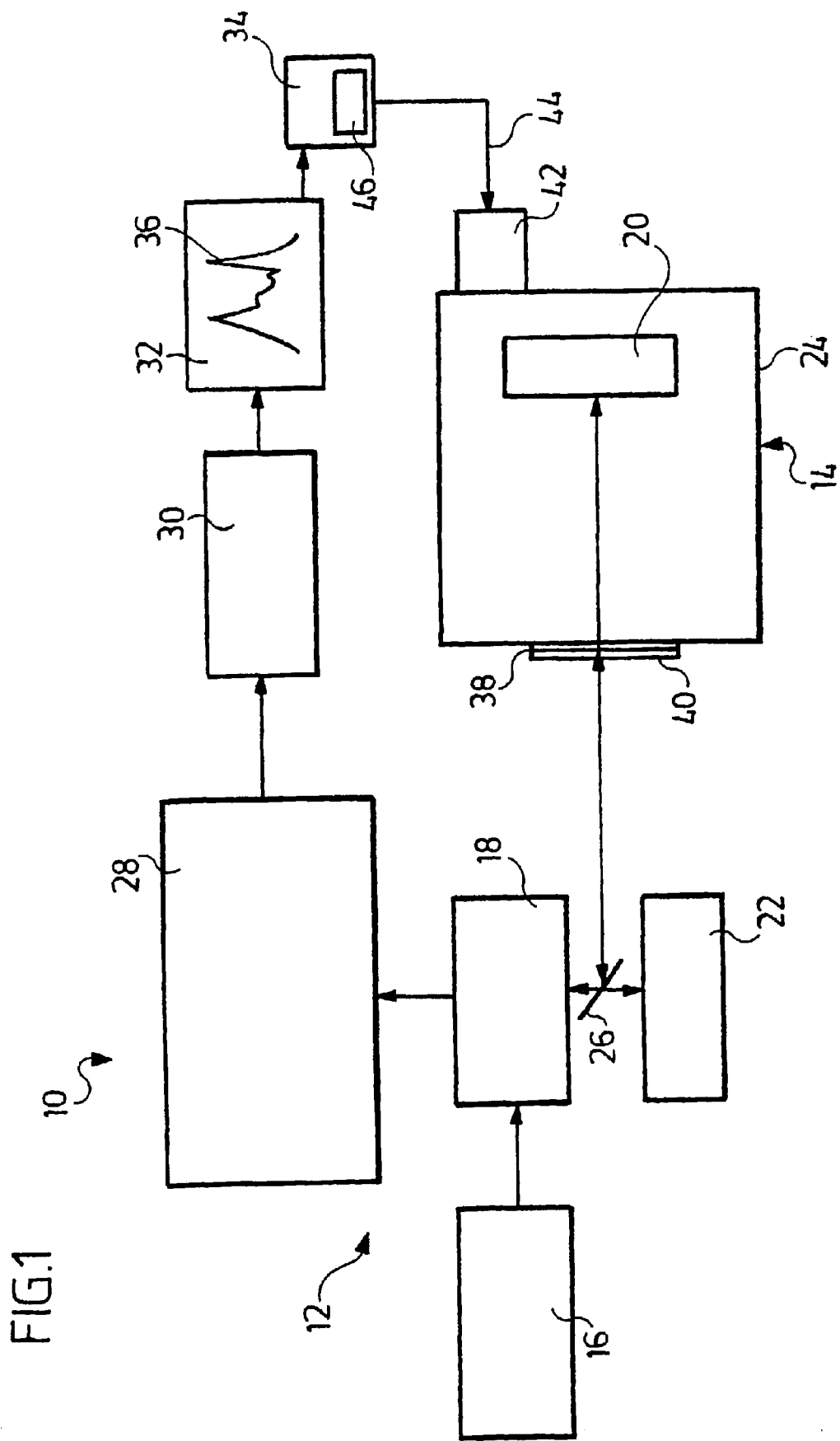

Woehl, G., et al., "Fully Relaxed $Si_{0.7}Ge_{0.3}$ Buffers Grown on Patterned Silicon Substrates for Hetero–cmos Transistors," submission to *Journal of Materials Science* (2001).

Woehl, G., et al., "Relaxed $Si_{0.7}Ge_{0.3}$ Buffer Layers Grown on Patterned Silicon Substrates for SiGe n–channel HMOS-FETS," *Thin Solid Films* 369 (2000), pp. 175–181.

Woehl, G., et al., "Fully Relaxed $Si_{0.7}Ge_{0.3}$ Buffers Grown on Patterned Silicon Substrates for Hetero–CMOS Transistors", *Journal of Materials Science: Materials in Electronics*, 12 (2001), pp. 235–240.

* cited by examiner

METHOD OF ANALYZING SILICON-GERMANIUM ALLOYS AND APPARATUS FOR MANUFACTURING SEMICONDUCTOR LAYER STRUCTURES WITH SILICON-GERMANIUM ALLOY LAYERS

The invention relates to a method for analyzing Si—Ge alloys, with which a Raman spectrum of a sample is recorded and Raman frequencies and Raman intensities of the Si—Si mode and the Si—Ge mode of the alloy layer are evaluated.

Components on a Si—Ge basis, such as, for example, infrared photodetectors, field effect transistors and photonic mixing detectors, are used, in particular, in optoelectronics. These components are optimized with respect to their properties, such as quantum efficiency at low dissipation power and low noise, essentially via the optimization of the Si—Ge alloy layers present. Optimization means in this respect that an alloy layer grows with a predetermined Ge content, for example, as buffer layer in as relaxed a manner as possible, i.e., is strained as little as possible or grows in a suitable and relaxed way.

It is known from the article "Raman scattering analysis of relaxed $GexSi_{1-x}$ alloy layers" of P. M. Mooney et al., Appl. Phys. Lett. 62 (17), 2069 (1993) for the portion of Ge in an alloy layer to be ascertainable via the ratio of the integrated intensities of the Si—Si mode to the Si—Ge mode.

The article "Measurements of alloy composition and strain in thin $Ge_xSi_{1-x}$ layers" of J. C. Tsang et al., J. Appl. Phys. 75 (12), 8098, 1994 describes, in particular, in conjunction with FIG. 6 therein a method as to how the specified intensities can be ascertained.

The Si—Si mode is attributable to phonon excitations on account of Si—Si oscillation movements, the Si—Ge mode to Si—Ge oscillation movements. In this respect, these are LO/TO phonons at k=0 in the crystalline SiGe.

Proceeding on this basis, the object underlying the invention is to improve the method of analysis specified at the outset such that any strain and any Ge portion in an alloy layer can be ascertained in a simple and as exact a manner as possible.

This object is accomplished in accordance with the invention, with the method specified at the outset, in that one or more spectrum contributions lying outside the Si—Ge modes and the Si—Si modes are evaluated as oscillation modes (i.e. vibration modes).

Intermediate modes and/or additional modes in Si cover layers or Si intermediate layers are not, therefore, considered as background in accordance with the invention but rather as a specific spectrum contribution. In accordance with the invention, the Raman spectrum is, when fitted, composed of a plurality of mode lines, namely, in particular, of the Si—Si mode, the Si—Ge mode, the intermediate modes and the cover layer modes and/or intermediate layer modes. As a result, on the other hand, the line profiles relevant for determining the strain via the shift in the Raman frequency and the line profiles required for determining the Ge concentration can be read selectively from the spectrum. Therefore, an optimized peak profile analysis may be carried out by means of the inventive method of analysis in order to obtain profile and position of the Si—Si mode and Si—Ge mode with minimum error.

Furthermore, the influence of lattice dislocations, cover layers and intermediate layers may be ascertained explicitly in order to obtain in this way an exact profile of the Si—Si mode and Si—Ge mode.

Complex Si—Ge alloy layers, which comprise a Si cover layer in addition to a Si—Ge alloy layer or corresponding layer sequences and/or one or more inserted Si intermediate layers which can, in particular, also be strained, may, in particular, be analyzed in accordance with the invention. The Si—Si mode of a cover layer or intermediate layer has a different frequency position to the Si—Si mode of a Si—Ge alloy layer. As a result of the inventive procedure, the profile and the peak position of the Si—Si mode and the Si—Ge mode may be determined with great precision even with the presence of such cover layers or intermediate layers in order to, on the other hand, be able to carry out a concentration analysis of Ge and relaxation determination.

As a result of the inventive method of analysis, a Raman spectrum can, in particular, be evaluated very quickly, i.e., the corresponding results of analysis are available very quickly. As a result, it is possible, on the other hand, to carry out measurements at short time intervals. A layer which has been produced may, in particular, be analyzed instantaneously during a coating process. As a result, it is, again, possible to influence the coating process accordingly in order to obtain an optimized overgrowth of layers on a substrate.

The intermediate modes are, in particular, local Si—Si oscillation modes. The above-mentioned Si—Si mode is brought about by way of Si—Si movement in the Si—Ge alloy. The above-mentioned Si—Ge mode is brought about by way of the Si—Ge movement in the Si—Ge alloy. These are bulk modes, wherein bulk modes are used in this case without any particular designation. The intermediate modes are, in particular, local Si—Si modes which result due to compositional dislocations. The phonon structure is modified by deviations from the perfect crystal lattice or due to defects. They have, in this case, an addition, such as, for example, "local" mode. Cover layers and intermediate layers (in particular, consisting of Si) also have a phonon structure which differs from that of a Si—Ge alloy layer.

The Si—Si mode and the Si—Ge mode are fitted, in particular, by way of an asymmetric curve. An intermediate mode is, on the other hand, fitted by way of a symmetric curve.

A reliable and rapid analysis of a Si—Ge alloy layer may be achieved when a fit spectrum which consists of a plurality of individual fit curves is fitted to the measured spectrum. In this respect, each individual fit curve is, in particular, a symmetric curve and, in addition, it is favorable when each individual fit curve is a Gauss-Lorentz curve. A Gauss-Lorentz curve thereby consists of the product of a Lorentz curve and a Gaussian curve.

It has proven to be advantageous when the Si—Si mode is fitted by way of three individual fit curves while the Si—Ge mode is fitted by way of two individual fit curves.

It has, furthermore, proven to be advantageous when an intermediate mode is fitted by way of a single fit curve.

As a result of such fits a fit spectrum is obtained which has minimal errors, for example, ascertained via a $\chi^2$ test, in relation to the measured spectrum. The parts, in particular, of the Si—Si mode and the Si—Ge mode of the alloy may, in particular, be separated out from such a spectrum in order to be able to carry out a rapid and reliable evaluation.

Furthermore, a background is deducted from the measured spectrum in order to eliminate parts of the spectrum not caused by Raman scattering (and, in particular, parts of the spectrum caused by Rayleigh scattering).

A concentration x of Ge in the Si—Ge alloy is determined in accordance with the formula $$\frac{I(Si-Si)}{I(Si-Ge)} = A\frac{1-x}{2x},$$

wherein I(Si—Si) is the integrated intensity of the Si—Si mode, I(Si—Ge) is the integrated intensity of the Si—Ge mode and A is a parameter dependent on the Raman spectroscopy device. This formula is also designated as Mooney formula. The Ge content in a Si—Ge alloy layer may be determined by means of this formula from measured parameters, namely the profiles of the corresponding modes, and also optimized accordingly. The profile of the relevant modes may, on the other hand, be determined by the inventive method of analysis in a reliable and exact manner, namely at short time intervals. As a result, an "in situ determination" of the Ge concentration is possible. The degree of relaxation within a Si—Ge layer may, on the other hand, be determined from the Ge concentration ascertained and the ascertainment of the strain via the ascertainment of the shift in frequency of the Si—Si mode.

The parameter A may be determined from comparative measurements, such as SIMS, XRD or EDX. As a result, a specified Raman spectroscopy device may, again, be calibrated in order to facilitate the direct determination of the Ge content of an alloy layer from the intensity ratios measured.

A strain and/or relaxation in the Si—Ge alloy is determined, in particular, by a shift in the Raman frequency, in particular, of the Si—Si mode in relation to a reference frequency. The reference frequency of the Si—Si mode is located at a wave number of 520.8 cm$^{-1}$ and corresponds to the Si—Si mode in the case of unstrained bulk Si material.

The invention relates, in addition, to a method of diagnosing Si—Ge alloys during their manufacture, with which the Raman spectrum is analyzed in a timed sequence during the manufacturing process with the method of analysis in accordance with any one of claims 1 to 17.

In this respect the manufacturing process is controlled, in particular, in accordance with the result of analysis.

In accordance with the invention, the Si—Ge alloy layer is therefore analyzed with respect to strain and Ge content at the same time via the analysis of the Raman spectrum of the Si—Ge alloy layer. Depending on the result, parameters of the manufacturing process can then be fitted in order to optimize the average overgrowth process of layers with respect to the intended use of the semiconductor structure.

The invention relates, in addition, to an apparatus for manufacturing semiconductor layer structures with Si—Ge layers.

In this respect, the object is to provide an apparatus with which optimized semiconductor components on a Si—Ge basis can be produced.

This object is accomplished in accordance with the invention in that the apparatus comprises:

an epitaxy device for the epitaxial overgrowth of layers with a control device for controlling and/or regulating the manufacture of the layers;

a Raman spectroscopy device for determining the Raman spectrum of a manufactured layer;

alternatively a timer for determining and/or evaluating the Raman spectrum at timed intervals and an evaluating device, by means of which the Raman spectrum can be evaluated in accordance with the method according to any one of claims 1 to 17.

The manufacturing process of a layer may be carried out by means of such an apparatus on the basis of an analysis of the coating process, i.e., the strain of a Si—Ge alloy layer and its Ge content may be determined in situ. This result may, again, be used to optimize the further build up of the layer in that the coating parameters are fitted accordingly in order to control the further build up of the coating.

It is of advantage, in particular, when the evaluating device is coupled to the epitaxy device such that the manufacture of the layer can be controlled and/or regulated via a result of analysis of the Raman spectrum.

For this purpose, the evaluating device makes one or more control signals available for the control device of the epitaxy device, i.e., the coating procedure may be controlled by means of the corresponding control signals.

Figure 2:
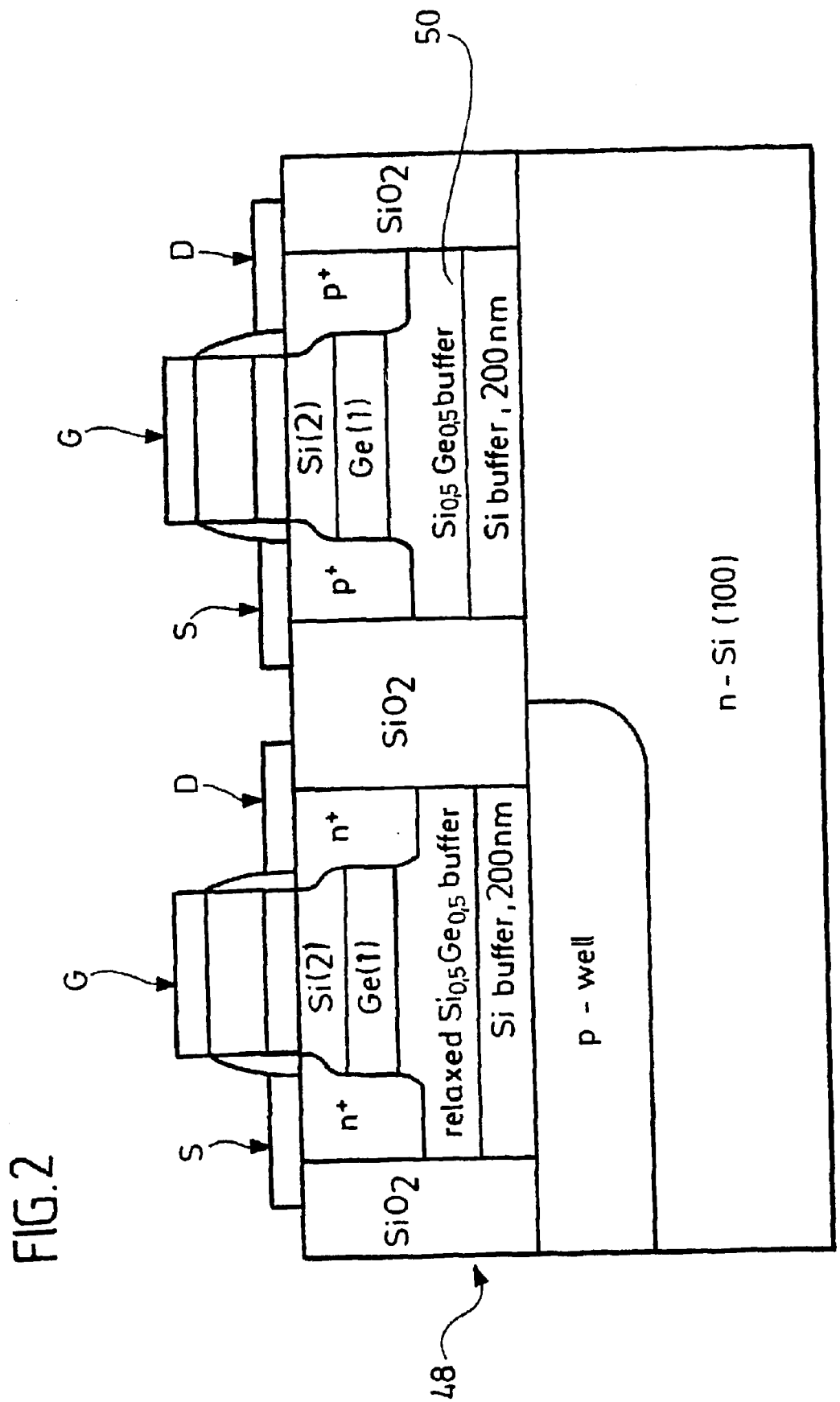
Figure 3:
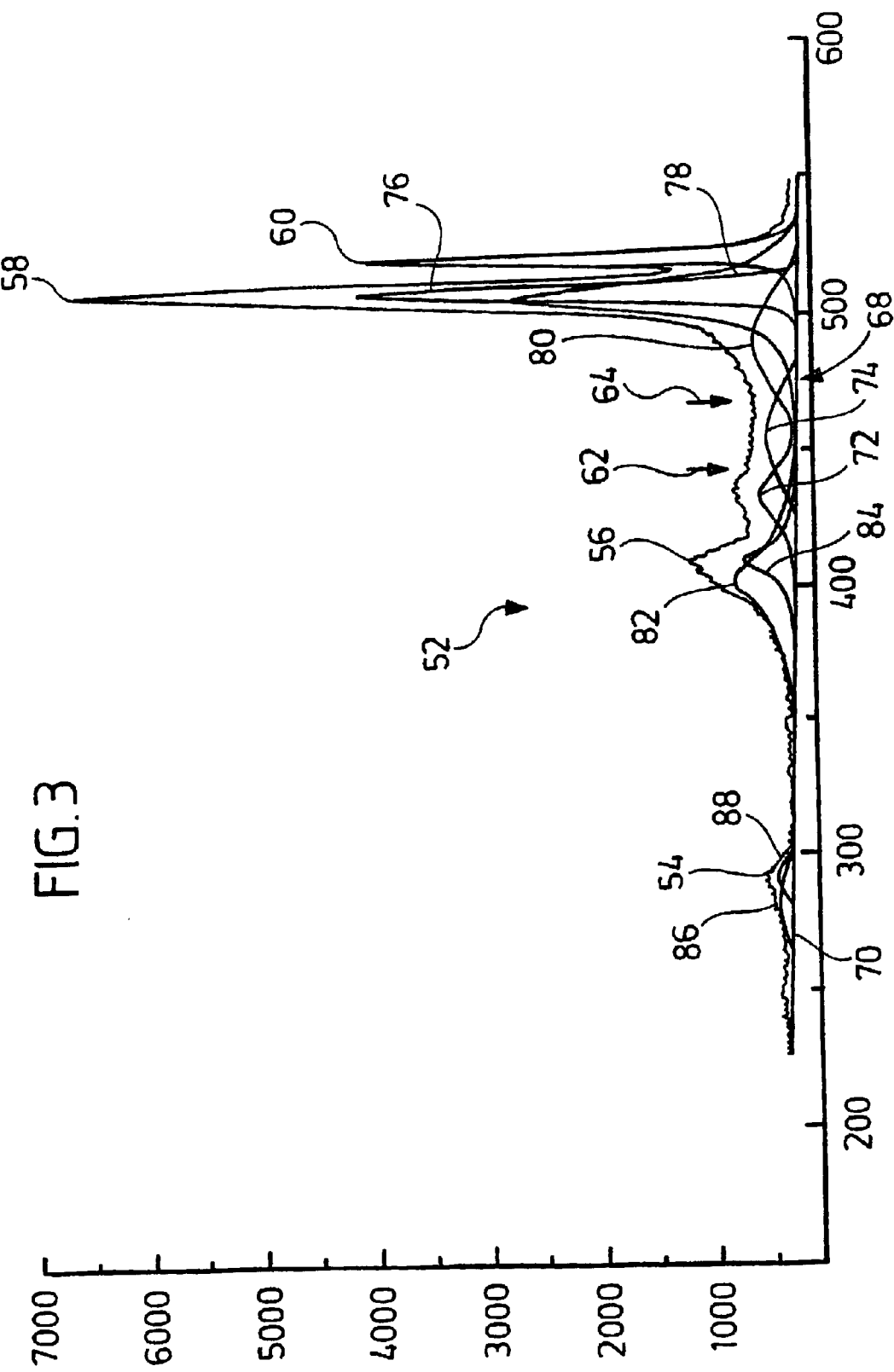
Figure 4:
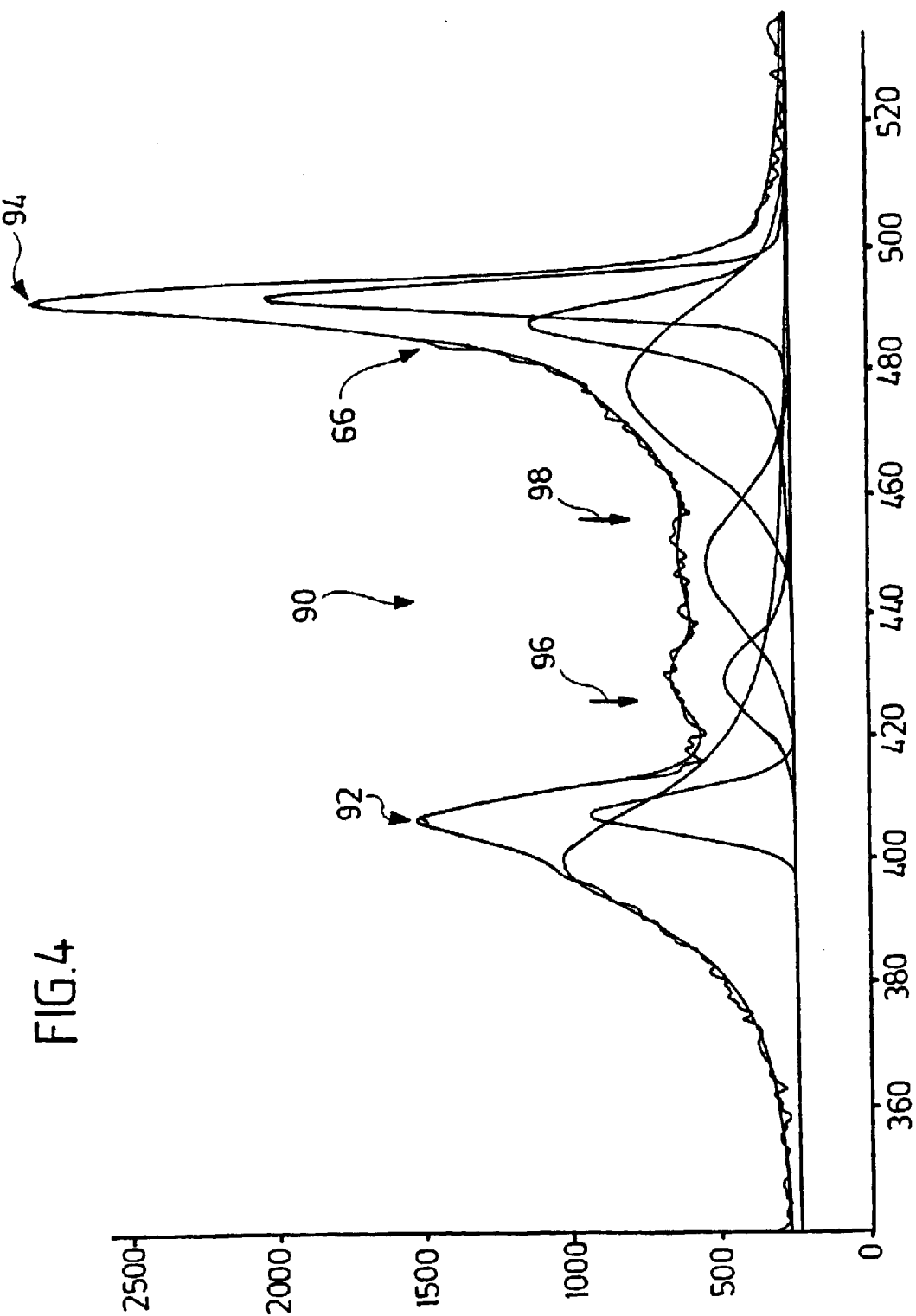
Figure 5:
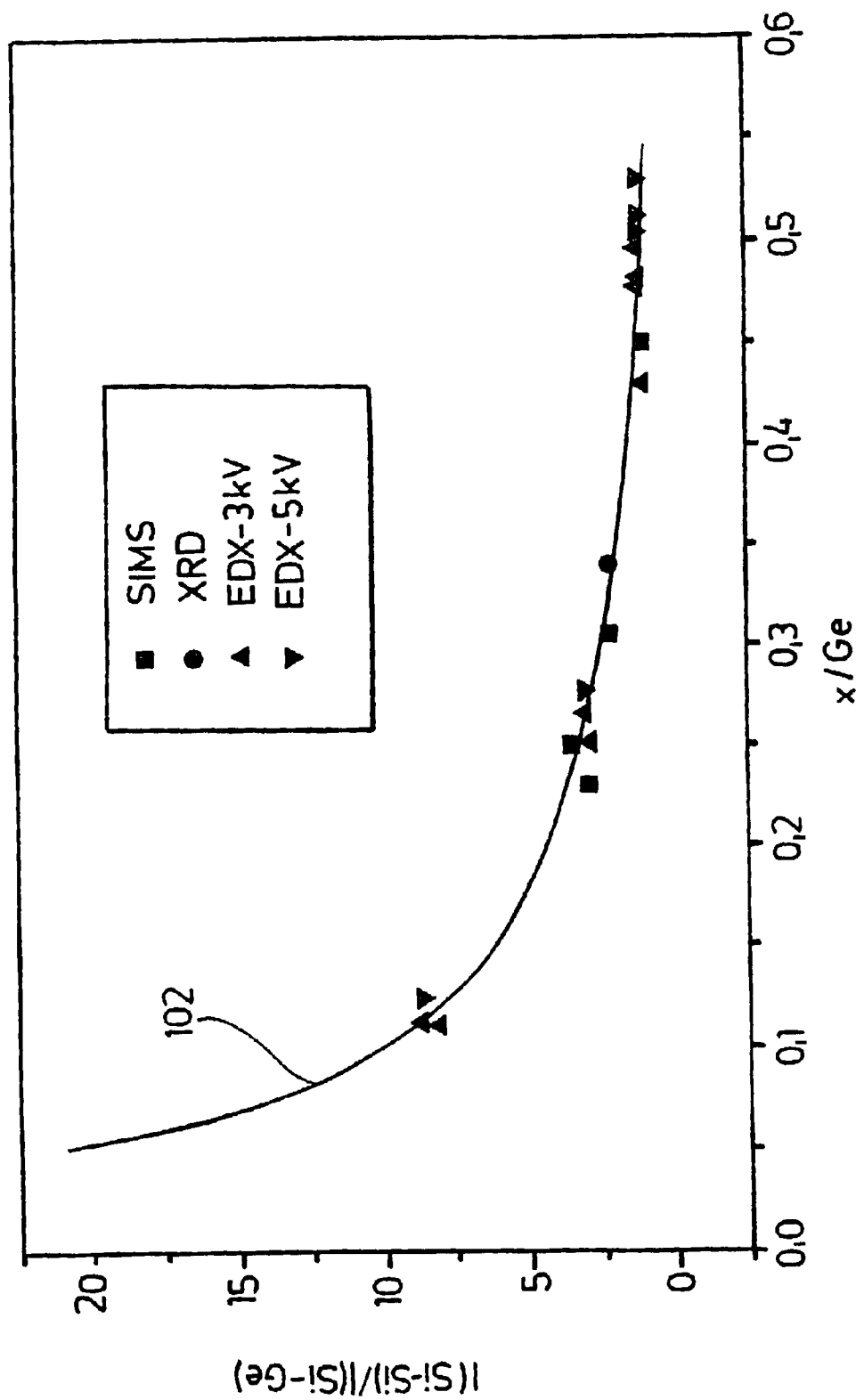

The following description of a preferred embodiment serves to explain the invention in greater detail in conjunction with the drawings. These show:

FIG. 1 a schematic view of a Raman spectroscopy device which is coupled to an epitaxy device;

FIG. 2 a schematic sectional view of a semiconductor layer structure in the form of a silicon-germanium hetero-MOSFET with a strain-reduced buffer, grown on a sample substrate;

FIG. 3 a first example of a Raman spectrum of a sample which has a silicon cover layer;

FIG. 4 a second example of a Raman spectrum of a sample without a silicon cover layer and FIG. 5 the dependence of the ratio of the integrated intensities of the silicon—silicon mode to the silicon-germanium mode on the germanium portion in the alloy.

An apparatus for manufacturing semiconductor layer structures with silicon(Si)-germanium(Ge) alloy layers, which is shown schematically in FIG. 1 and designated as a whole as 10, comprises a Raman spectroscopy device 12 and an epitaxy device 14.

The Raman spectroscopy device 12 has as excitation light source a laser 16, for example, a helium-cadmium laser. A typical excitation wavelength is, in this respect, 441.6 nm; the optical penetration depth in a semiconductor layer is in the order of magnitude of 300 nm. An excitation light beam of the laser 16 is directed via a telescope or confocal microscope 18 onto a sample 20 and 22, respectively. The sample 20 is, in this respect, arranged in an epitaxy chamber 24 of the epitaxy device 14.

Alternatively, it may be provided for the sample (reference numeral 22 in FIG. 1) to be arranged outside the epitaxy chamber 24. It may, in particular, be provided for the apparatus 10 to allow the possibility of examining a sample 20 within the epitaxy chamber 24 or examining a sample 22 outside it. A corresponding change-over can, for example, be carried out via the positioning of a mirror 26 in the excitation beam coming from the telescope or the confocal microscope 18 in order to direct this excitation beam either onto the location of the sample 22 or onto the location of the sample 20 in this way.

The telescope or the confocal microscope 18 is designed, in particular, in such a manner that the excitation beam is imaged on the sample 20 and 22, respectively, with a low but still adequate power in a beam diameter of, for example, 1 $\mu$m. As a result, a considerable heating up of the sample at the location of the excitation light beam can be prevented.

The Raman scattered light emitted by the sample 20 or 22, caused by the excitation with the laser 16, is registered during back-scattering with a suitable Raman spectrometer 28 and recorded with a CCD camera 30 and shown, for example, on a screen 32.

The corresponding Raman spectrum 36 is analyzed in an evaluating device 34 and the relevant parameters, such as Ge part x, the strain and the degree of relaxation, are ascertained.

The excitation light beam is coupled via a window 38 into the epitaxy chamber 24 which is, in particular, a vacuum chamber. Unwanted light emissions, for example, in the visible wavelength range or also near-infrared radiation, such as heat radiation of the epitaxy chamber 24, may be filtered out via an optical filter 40 for the back-scattered radiation of the probe 20 in order to reduce the background noise for the CCD camera 30 in this way.

The manufacturing process of a sample 20 in the epitaxy chamber 24 is controlled and/or regulated via a control device 42. The control or regulating parameters thereby depend on the specific coating method. For example, the pressure in the epitaxy chamber 24 is controlled during the chemical vapor epitaxy (CVE) and a substrate temperature of the substrate to be coated. During the molecular beam epitaxy (MBE) the beam may be controlled accordingly.

The evaluating device 34 is connected to the control device 42 of the epitaxy device 14 via a control line 44 so that data obtained from the evaluation of a Raman spectrum 36 can be used for controlling the coating process in the epitaxy chamber 34. It is provided, in particular, for in-situ diagnostics of the coating process of the probe 20 to be carried out, i.e., for the current coating result to be checked temporarily and the corresponding coating parameters to be altered depending on the result of the check for optimizing the layer, insofar as this is required.

The evaluating device 34 has a timer 44 for the timed control of the coating process in the epitaxy chamber 24, this timer transmitting the result of analysis of the Raman spectrum 36 which has just been recorded to the control device 42 at predetermined timed intervals in order to obtain a time-resolved analysis of the coating result and, in particular, to be able to analyze the overgrowth of the layers of the sample 22 during this overgrowth process.

A semiconductor layer structure 48 is shown in FIG. 2 as an example of a sample 20 and this can be manufactured epitaxially. In this respect, it is a Si—Ge hetero-MOSFET with a strain-reduced buffer 50 consisting of a Si—Ge alloy. A source of the MOSFET according to FIG. 2 is designated with the reference numeral S, a gate with the reference numeral G and a drain with the reference numeral D.

In accordance with the invention, the Si—Ge alloy layer 50 may be analyzed during the manufacture or the manufacturing process may be optimized by means of analysis of a manufactured layer such that this layer is relaxed to a great extent. As a result of the fact that strains are then minimized within such a layer 50, the properties of a corresponding semiconductor component may, again, be optimized.

A first example of a Raman spectrum 52 of a Si—Ge alloy layer is shown in FIG. 1, wherein the intensity is plotted over the wave number (unit $cm^{-1}$). The Raman spectrum mirrors the phonon structure of the Si—Ge alloy layer. As a result, the strain or the degree of relaxation within the alloy layer can be ascertained from the Raman spectrum. The portion of Ge in the alloy layer can also be determined via the relative portions of the corresponding modes. In this respect, the Stokes part of the Raman spectrum is evaluated.

A Ge—Ge mode 54 is apparent in the Raman spectrum 52 and this is attributable to the phonon excitations on account of Ge—Ge oscillation movements. The associated phonon branch is the LO/TO branch and the wave vector is at k≈0. A Si—Ge mode 56 is to be found at a higher wave number (higher energy) and this is attributable to the phonon excitation due to Si—Ge oscillation movements.

Furthermore, a Si—Si mode 58 is apparent which results due to the Si—Si oscillation movement.

A line 60 is apparent, in addition, in the Raman spectrum 52 and this likewise represents a Si—Si mode but in a cover layer which is not a component of the alloy. This line 60 is not, therefore, caused by the Si—Ge alloy layer and must therefore be left out of consideration during the evaluation of the Si—Ge layer. (This line 60 must be taken into account insofar as it is to be deducted from the spectrum 52 in order to be able to determine the mode 58 correctly).

The modes designated above as Ge—Ge mode (reference numeral 54), Si—Ge mode (reference numeral 56) and Si—Si mode (reference numeral 58) are bulk modes, i.e., caused by the three-dimensional lattice structure in the Si—Ge alloy layer. Apart from these, local Si—Si modes can, however, also exist, as indicated in the Raman spectrum 52 by the arrows 62 and 64. These local Si—Si modes 62, 64 result on account of growth imperfections, such as lattice defects. These local modes 62, 64 are to be taken into consideration accordingly for the correct evaluation of the Raman spectrum 52 with respect to determining the properties of the Si—Ge alloy layer to be analyzed, i.e., their portion in the Raman spectrum 52 is to be determined in order to, on the other hand, be able to ascertain the modes 56 and 58 with respect to peak position and profile as exactly as possible. In accordance with the invention, these local modes 62, 64 are evaluated as oscillation modes in order to be able to ascertain their portion in the spectrum and, therefore, their influence on the resonance curves 56, 58 in this way.

Excitation modes which are attributable to additional Si layers, such as cover layers or intermediate layers, are treated in the same way in order to determine their influence on the peak position and profile of the modes 56, 58 and, therefore, to ensure as exact an ascertainment as possible of the Si—Si mode 58 and the Si—Ge mode 56 from the Raman spectrum.

The position of the Si—Si mode 58 is determined by the strain of the Si—Ge alloy layer. In the case of a pure, unstrained Si sample (without Ge portion), this mode is at a wave number of 520.8 $cm^{-1}$. In the Raman spectrum 52, this mode is at a wave number of approximately 500 $cm^{-1}$; the alloy layer is therefore strained, wherein the distance from the specified reference wave number of 520.8 $cm^{-1}$ is a measure for the strain: The greater the strain, the greater this distance.

The portion x of Ge in a Si—Ge layer may be derived from the formula $$\frac{I(Si-Si)}{I(Si-Ge)} = A\frac{1-x}{2x},$$

wherein I(Si—Si) is the integrated intensity of the Si—Si mode 58 and I(Si—Ge) is the integrated intensity of the Si—Ge mode 56. The parameter A is determined by the properties of the Raman spectroscopy device 12 and by the wavelength of the excitation light of the laser 16. One possibility for determining this parameter A is specified below. The above-mentioned formula is also designated as Mooney formula, cf. in this respect, for example, P. M. Mooney et al., "Raman scattering analysis of relaxed $Ge_xSi_{1-x}$ alloy layers", Appl. Phys. Lett. 62(17), 2069 (1993).

It is, therefore, necessary to determine the line profile of the Si—Si mode 58 and the line profile of the Si—Ge mode in order to be able to calculate the integrated intensities. For this purpose, the portion which does not belong to the specified modes 56 and 58 is, again, to be ascertained from the Raman spectrum 52 in order to be able to determine these modes as exactly as possible. The mode frequency of the Si—Si mode 58 which characterizes the strain is determined by the peak position.

In accordance with the invention, the Raman spectrum 52 is now fitted by a fit spectrum 66 (cf. FIG. 4; in this case a sample without any Si cover layer has been examined). The fit spectrum 66 is formed by a plurality of fit curves 68 which are Gauss-Lorentz curves, i.e., the product of a Lorentz curve and a Gaussian curve. During the fitting of the measured spectrum 52 to the fit spectrum 66, a background 70 is deducted first of all and this is determined, in particular, by an area between the measured spectrum sufficiently below the Ge—Ge mode 54 and sufficiently above the Si—Si mode 58. The Si—Si mode 60 on account of a Si cover layer (or a Si intermediate layer) is separated out via a single fit curve.

If several such cover layers and/or intermediate layers are located in a sequence of Si—Ge alloy layers, the Raman spectrum displays the corresponding contributions. During the evaluation, these contributions are treated as described above, i.e., respectively fitted by a single Gauss-Lorentz curve.

The local modes 62, 64 are likewise fitted by corresponding fit curves 72, 74, namely each by a single Gauss-Lorentz curve.

The Si—Si mode 58 is fitted by way of three fit curves 76, 78, 80 which are offset relative to one another so that an asymmetric line profile is obtained.

The Ge—Ge mode 54 is likewise fitted by means of an asymmetric line profile, wherein this fit is brought about via two offset fit curves 82, 84.

The Ge—Ge mode 54 is likewise fitted via two fit curves 86, 88.

The parameters of the respective Gauss-Lorentz curves as fit curves are adjusted such that the best result for the fit spectrum 66 in comparison with the measured Raman spectrum 52 results, for example, via a X minimizing test.

The fitted Si—Si mode 58 and Si—Ge mode 56 may then be determined by way of the fit described, i.e., formation of the fit spectrum 66 by way of superposition of a plurality of Gauss-Lorentz curves, wherein the additional spectrum contributions are taken into account. The position (peak) of the modes 56, 58 may be determined with great accuracy by means of such a peak-profile analysis and, in addition, the profile may be determined with great accuracy and, as a result, the integrated intensity ascertained in order to be able to determine the Ge portion in a Si—Ge layer via the Mooney formula.

This peak-profile analysis may be carried out with conventional analysis programs, such as, for example, PEAKSOLVE of Gaiactic Ind. Corp., wherein the preliminary information is put in that Gauss-Lorentz curves are to be applied accordingly as fit curves, that a respective fit curve is to be applied for local Si—Si modes 62, 64, that three fit curves are to be applied for the Si—Si mode 58 and that two fit curves are to be applied for the Si—Ge mode 56.

The necessary information for analyzing the Si—Ge alloy layer can then be ascertained in a quick and exact way.

In a further example of a Raman spectrum 90, which is shown in FIG. 4 in sections with a Si—Ge mode 92, a Si—Si mode 94 and local Si—Si modes 96, 98, such a fit has likewise been carried out. In the case of the sample analyzed, no Si cover layer was present. The Si—Si mode 94 was, again, fitted by way of three fit curves and the Si—Ge mode 92 by way of two fit curves. The local Si—Si modes 96, 98 were fitted by one fit curve each. It is apparent from FIG. 2 that an excellent congruence prevails between the measured spectrum 90 and the fit spectrum 66.

The parameter A may be determined from comparative measurements, via which the Raman spectroscopy device 12 can be calibrated accordingly. In FIG. 5, the ratio of the intensities included in the Mooney formula is shown as a function of the Ge concentration x in a Si—Ge alloy layer. The curve 102 corresponds to the Mooney formula. Measuring points are inserted for samples examined by means of secondary ion mass spectroscopy (SIMS), x-ray diffraction (XRD) or energy-dispersive x-ray scattering (EDX). With a corresponding selection of the parameter A, the curve 102 results due to the measuring points. A fit has thereby resulted in A=2.2. On the basis of this known A, the Ge content in a Si—Ge alloy layer may, on the other hand, be determined from the Raman spectra in accordance with the Mooney formula.

The degree of relaxation of the alloy can also be determined from the simultaneous determination of the strain (via the shift in the Raman frequencies) and the Ge concentration in the Si—Ge alloy layer in accordance with the formula $$\gamma = \frac{\Delta\omega_1 - \Delta\omega}{\Delta\omega_1(x) - \Delta\omega_2(x)},$$

wherein $\Delta\omega$ is the ascertained shift in frequency of the Si—Si mode 58 and 94, respectively, in relation to the reference mode, $\Delta\omega_1(x)$ is a shift in a biaxially strained, pseudomorphic layer with the Ge concentration x and $\Delta\omega_2(x)$ is a shift in the unstrained, alloy-like layer with the Ge concentration x. Cf. in this respect B. Dietrich et al., "Raman investigations of elastic strain relief in $Si_{1-x}Ge_x$ layers on patterned silicon substrate", J. Appl. Phys. 74 (12), 7223 (1993).

In accordance with the invention, the content x of Ge in a Si—Ge alloy layer may therefore be determined in a quick and exact manner from a measured Raman spectrum 52 and 90, respectively. Furthermore, the shifts in frequency may be ascertained and the degree of relaxation may, on the other hand, be determined therefrom.

Since the specified analyses and diagnoses can be carried out very quickly, the corresponding results may be obtained during the coating of a sample 20 in order to be able to modify the corresponding parameters of the epitaxy process via the control device 42 in the case of deviations from a desired result such that the build up of layers is optimized and, therefore, the properties of the component to be manufactured are optimized.

It is possible, in addition, to analyze a semiconductor structure during or after its manufacture and, in particular, during the epitaxy process in order to make, for example, assertions as to whether a layer is relaxed enough or not, i.e., to make assertions as to whether the structure manufactured is to be thrown away or can be used further.

What is claimed is:

1. Method of analyzing Si—Ge alloys, comprising the steps of:
   recording a Raman spectrum of a sample; and
   evaluating Raman frequencies and Raman intensities of the Si—Si modes and the Si—Ge modes of the alloy layer;
   wherein one or more spectrum contributions lying outside the Si—Ge modes and the Si—Si modes are evaluated as vibration modes.

2. Method of analysis as defined in claim 1, wherein spectrum contributions of local Si—Si modes are evaluated as vibration modes.

3. Method of analysis as defined in claim 1, wherein spectrum contributions of Si cover layers or Si intermediate layers are evaluated as vibration modes.

4. Method of analysis as defined in claim 1, wherein the Si—Si modes and the Si—Ge modes are fitted by means of an asymmetric curve.

5. Method of analysis as defined in claim 1, wherein an intermediate mode is fitted by means of a symmetric curve.

6. Method of analysis as defined of claim 1, wherein a fit spectrum is fitted to the recorded spectrum, said fit spectrum consisting of a plurality of individual fit curves.

7. Method of analysis as defined in claim 6, wherein each individual fit curve is a symmetric curve.

8. Method of analysis as defined in claim 6, wherein each individual fit curve is a Gauss-Lorentz curve.

9. Method of analysis as defined in claim 6, wherein the Si—Si mode is fitted by way of three individual fit curves.

10. Method of analysis as defined in claim 6, wherein the Si—Ge mode is fitted by way of two individual fit curves.

11. Method of analysis as defined in claim 1, wherein an intermediate mode is fitted by way of a single fit curve.

12. Method of analysis as defined in claim 1, wherein a background is deducted from the recorded spectrum.

13. Method of analysis as defined in claim 1, wherein a concentration of Ge in the Si—Ge alloy is determined in accordance with $$\frac{I(Si-Si)}{I(Si-Ge)} = A\frac{1-x}{2x},$$

wherein I(Si—Si) is the integrated intensity of the Si—Si mode, (Si—Ge) is the integrated intensity of the Si—Ge mode and A is a parameter dependent on the Raman spectroscopy device.

14. Method of analysis as defined in claim 13, wherein the parameter is determined from comparative measurements with other methods of measurement.

15. Method of analysis as defined in claim 1, wherein strain and/or relaxation in the Si—Ge alloy is determined by a shift in the Raman frequency in relation to a reference frequency.

16. Method of analysis as defined in claim 15, wherein the reference frequency of the Si—Si mode is located at a wave number of 520.8 cm$^{-1}$.

17. Method of analysis as defined in claim 6, wherein a Si cover layer mode or Si intermediate layer mode is fitted by way of a single fit curve.

18. Method of diagnosing Si—Ge alloys during their manufacture, comprising the steps of:

analyzing the Raman spectrum in a timed sequence during the manufacturing;

wherein:

the Raman spectrum of a sample is recorded and Raman frequencies and Raman intensities of the Si—Si modes and the Si—Ge modes of the alloy layer are evaluated, and one or more spectrum contributions lying outside the Si—Ge modes and the Si—Si modes are evaluated as vibration modes.

19. Method of diagnosis as defined in claim 18, wherein the manufacturing process is controlled in accordance with the result of analysis.

20. Apparatus for manufacturing semiconductor layer structures with Si—Ge alloy layers, comprising:

an epitaxy device for the epitaxial overgrowth of layers with a control device for controlling and/or regulating the manufacture of the layers;

a Raman spectroscopy device for determining the Raman spectrum of a manufactured layer; and an evaluating device, the Raman spectrum being evaluatable by means of said evaluating device by evaluating Raman frequencies and Raman intensities of the Si—Si modes and the Si—Ge modes of the alloy layer;

wherein one or more spectrum contributions lying outside the Si—Ge modes and the Si—Si modes are evaluated as vibration modes.

21. Apparatus as defined in claim 20, wherein the evaluating device is coupled to the epitaxy device such that the layer manufacture is controllable and/or regulatable via a result of analysis of the Raman spectrum.

22. Apparatus as defined in claim 21, wherein the evaluating device makes one or more control signals available for the control device of the epitaxy device.

23. Apparatus as defined in claim 21, characterized by a timer for determining and/ox evaluating the Raman spectrum at timed intervals.

* * * * *

UNITED STATES PATENT AND TRADEMARK OFFICE
CERTIFICATE OF CORRECTION

PATENT NO. : 6,744,501 B2
DATED : June 1, 2004
INVENTOR(S) : Klose

It is certified that error appears in the above-identified patent and that said Letters Patent is hereby corrected as shown below:

Column 9,
Line 1, after the word "claim", change "1" to -- 6 --.

Column 10,
Line 2, correct "and/ox" to read -- and/or --.

Signed and Sealed this

Sixteenth Day of November, 2004

JON W. DUDAS
*Director of the United States Patent and Trademark Office*